US011793476B2

United States Patent
Loustauneau et al.

(10) Patent No.: US 11,793,476 B2
(45) Date of Patent: *Oct. 24, 2023

(54) METHOD AND A SYSTEM FOR OBTAINING OPERATING PARAMETERS FOR X RAY DATA ACQUISITION

(71) Applicant: TROPHY, Croissy-Beaubourg (FR)

(72) Inventors: Vincent Loustauneau, Fontenay-sous-Bois (FR); Olivier Nesme, Nogent-sur-Marne (FR); Chloe Abdoul Carime Comparetti, Vincennes (FR); Colombe Maury, Marne-la-Vallee (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/592,825

(22) Filed: Feb. 4, 2022

(65) Prior Publication Data

US 2022/0361830 A1    Nov. 17, 2022

Related U.S. Application Data

(63) Continuation of application No. 16/652,030, filed as application No. PCT/EP2018/076173 on Sep. 26, 2018, now abandoned.

(30) Foreign Application Priority Data

Sep. 29, 2017 (FR) .................................. 17306307.4

(51) Int. Cl.
*A61B 6/03* (2006.01)
*A61B 6/06* (2006.01)
(Continued)

(52) U.S. Cl.
CPC ................ *A61B 6/14* (2013.01); *A61B 6/032* (2013.01); *A61B 6/04* (2013.01); *A61B 6/06* (2013.01);
(Continued)

(58) Field of Classification Search
CPC .. A61B 6/14; A61B 6/032; A61B 6/04; A61B 6/06; A61B 6/4085; A61B 6/469;
(Continued)

(56) References Cited

U.S. PATENT DOCUMENTS

2015/0190102 A1* 7/2015 Bruno .................... A61B 6/542
378/39

* cited by examiner

*Primary Examiner* — Courtney D Thomas

(57) ABSTRACT

The invention concerns a method for obtaining operating parameters for x-ray imaging a patients maxillofacial region, the method comprising: —identifying a patients maxillofacial first region of interest ROI1, —determining a height of a horizontal plane of said patients maxillofacial first region of interest ROI1 when the patient is in an occlusion position or bites a patient positioning accessory, said horizontal plane passing through the teeth and the bones of the jaw, —acquiring through a slit-shaped collimator window a first set of data relative to said patients maxillofacial first region of interest ROI1 including the horizontal plane using x-ray CBCT imaging and a first x-ray dose, said first set of data being suitable for generating a CBCT slice, —reconstructing the CBCT slice comprising the horizontal plane based on the first set of data relative to the patients maxillofacial first region of interest ROI1, —obtaining operating parameters for an x-ray imaging apparatus based on the reconstructed CBCT slice in view of acquiring a second set of data of a patients maxillofacial second region of interest ROI2 using a second x-ray dose, the first x-ray dose being lower than the second x-ray dose.

19 Claims, 8 Drawing Sheets

(51) Int. Cl.
*A61B 6/00* (2006.01)
*A61B 6/14* (2006.01)
*A61B 6/04* (2006.01)

(52) U.S. Cl.
CPC .......... *A61B 6/4085* (2013.01); *A61B 6/5217* (2013.01); *A61B 6/542* (2013.01)

(58) Field of Classification Search
CPC ....... A61B 6/485; A61B 6/488; A61B 6/5217; A61B 6/542; A61B 6/0421; A61B 6/465; A61B 6/544; A61B 6/545; G16H 50/30
See application file for complete search history.

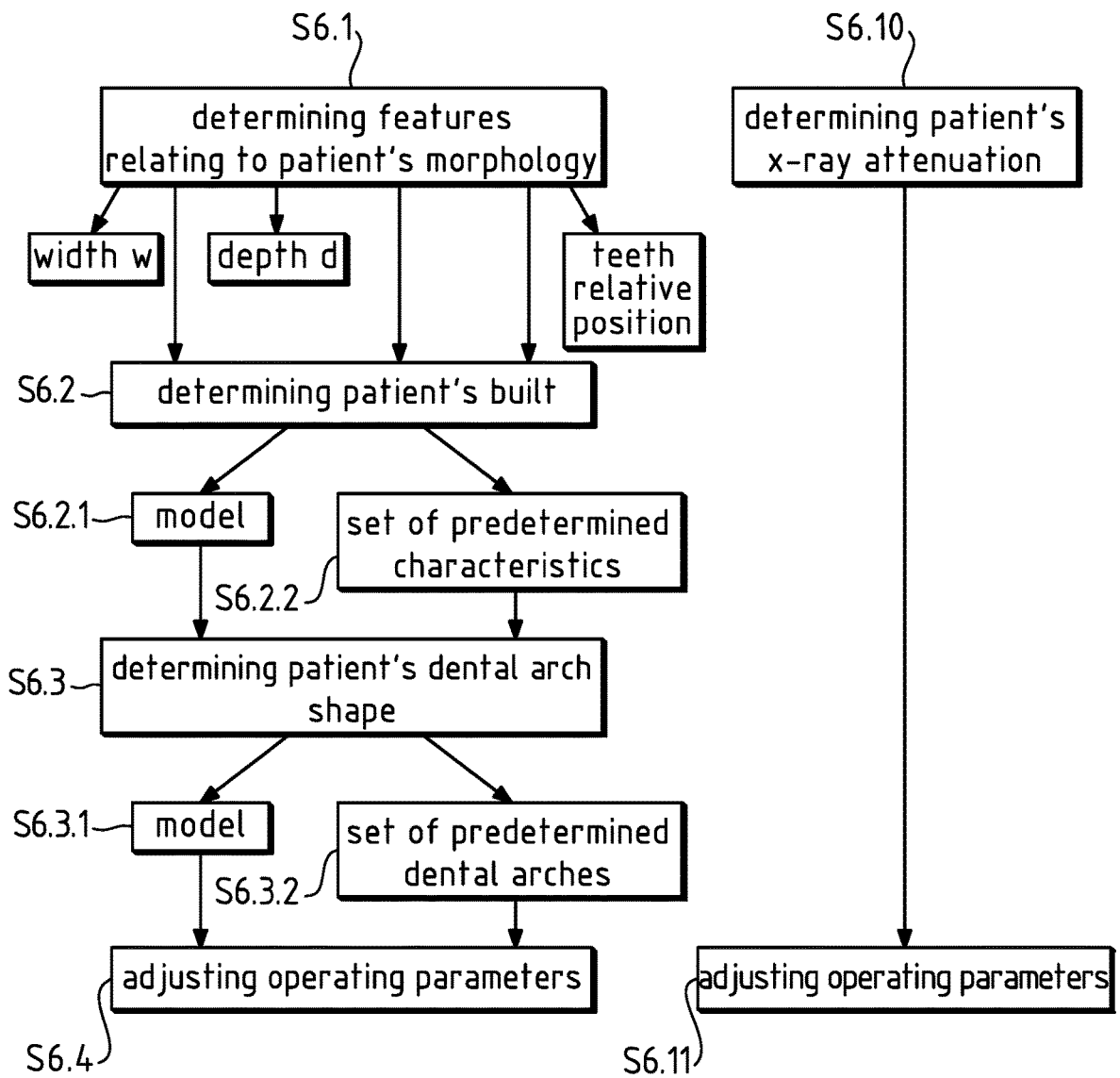

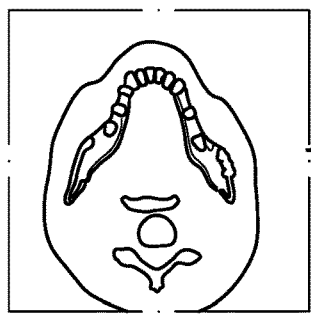
FIG.8A
FIG.8B
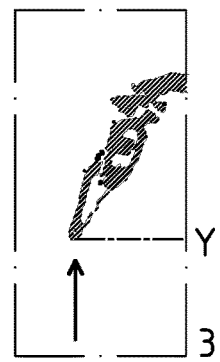
FIG.8C
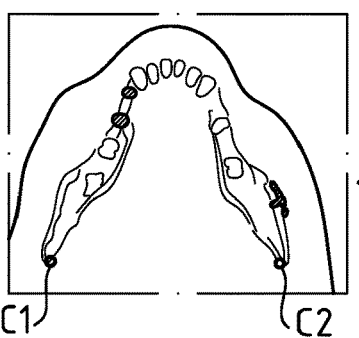
FIG.8D
FIG.8E
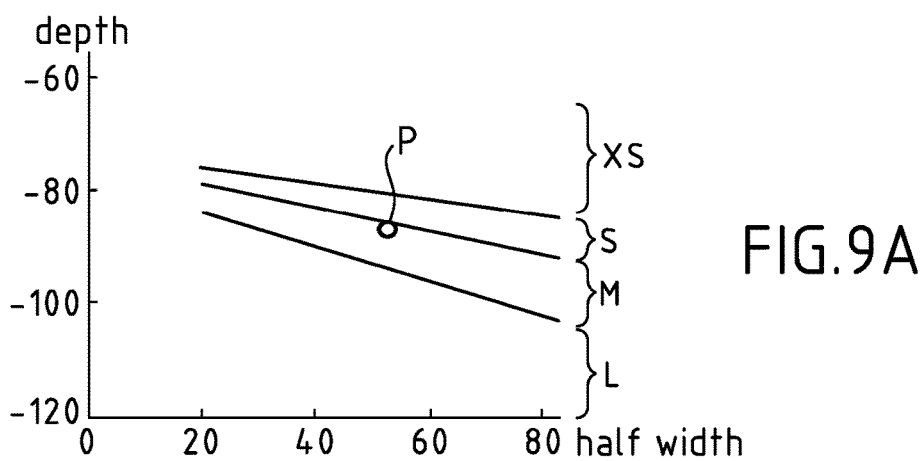
FIG.9A
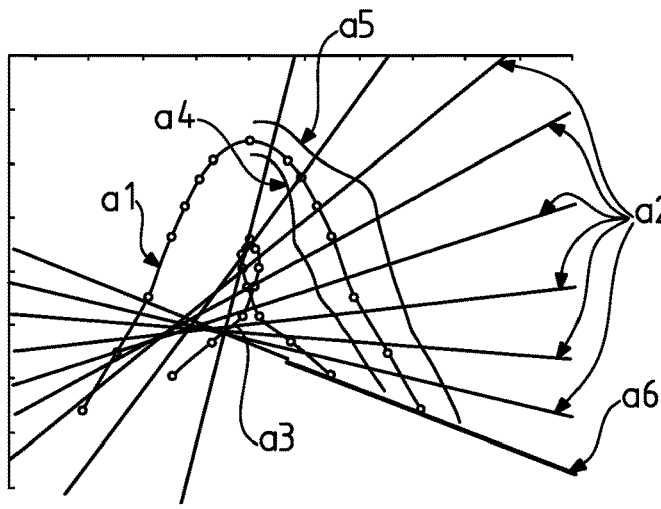
FIG.9B

METHOD AND A SYSTEM FOR OBTAINING OPERATING PARAMETERS FOR X RAY DATA ACQUISITION

TECHNICAL FIELD

The disclosure relates generally to the field of dental x-ray imaging and in particular to the field of x-ray CBCT (Cone Beam Computed Tomography) imaging. More specifically, the disclosure relates to a method for obtaining a radiographic image of a patient's maxillofacial region through x-ray data acquisition, an x-ray CBCT imaging interface system and an x-ray CBCT imaging apparatus.

BACKGROUND

Conventional methods and systems for obtaining a radiographic image of a patient's maxillofacial region through x-ray imaging require adjusting operating or acquisition parameters of the x-ray imaging apparatus used such as the x-ray dose, the exposure time to the x-ray dose, etc. depending on the patient morphology.
In this respect, the practitioner has to manually select in the interface of the program controlling the operation of the apparatus the build of the patient among a set of predefined patient's builds, the shape of the patient's arch among a set of predefined patient's arches, the bone density etc. so that the operating parameters of the apparatus be adapted to the patient.
While such methods and systems may have achieved certain degrees of success in their particular applications, there is nevertheless a need to improve these methods and systems.

SUMMARY

An object of the present disclosure is to provide a novel method and apparatus for obtaining or adjusting operating or acquisition parameters of an x-ray imaging apparatus before submitting a patient to an x-ray examination.
Another object of the present disclosure is to avoid unnecessary x-ray doses for the patients when undergoing an x-ray examination.
A further object of the present disclosure is to optimize the adjustment of operating or acquisition parameters of an x-ray imaging apparatus before submitting a patient to an x-ray examination.
A still further object of the present disclosure is to simplify the task of the practitioner when adjusting operating or acquisition parameters of an x-ray imaging apparatus. These objects are given only by way of illustrative example, and such objects may be exemplary of one or more embodiments of the invention. Other desirable objectives and advantages inherently achieved by the invention may occur or become apparent to those skilled in the art. The invention is defined by the appended claims.
According to one aspect of the disclosure, there is provided a method for obtaining operating parameters for x-ray imaging a patient's maxillofacial region, the method comprising:
identifying a patient's maxillofacial first region of interest ROI1,
determining a height of a horizontal plane of said patient's maxillofacial first region of interest ROI1 when the patient is in an occlusion position or bites a patient positioning accessory, said horizontal plane passing through the teeth and the bones of the jaw,
acquiring through a slit-shaped collimator window a first set of data relative to said patient's maxillofacial first region of interest ROI1 including the horizontal plane using x-ray CBCT imaging and a first x-ray dose, said first set of data being suitable for generating a CBCT slice,
reconstructing the CBCT slice comprising the horizontal plane based on the first set of data relative to the patient's maxillofacial first region of interest ROI1,
obtaining operating parameters for an x-ray imaging apparatus based on the reconstructed CBCT slice in view of acquiring a second set of data of a patient's maxillofacial second region of interest ROI2 using a second x-ray dose, the first x-ray dose being lower than the second x-ray dose.
The method according to an embodiment of the invention is a novel method which uses a first x-ray "shoot" with a first x-ray dose (low dose) to obtain and reconstruct a CBCT slice comprising the patient's maxillofacial first region of interest ROI1 from which operating parameters for an x-ray imaging apparatus are obtained. The first x-ray dose is lower than the second dose to be used with the obtained parameters since the CBCT slice does not need many details and the patient must not be too much exposed to x-rays. However, the CBCT slice information has to be sufficient to provide morphology information enabling obtaining of operating parameters. The information extracted from the CBCT slice being proper to the patient, it enables obtaining of operating parameters which are particularly adapted to the patient. The CBCT slice is generally a thin slice that includes the ROI1.
According to possible features or aspects:
determining a height of the horizontal plane of the patient comprises beforehand one of the following:
acquiring a lateral x-ray scout view comprising the patient's maxillofacial first region of interest (ROI1);
acquiring an optical image comprising the patient's maxillofacial first region of interest (ROI1) including landmarks;
performing physical measurements on the patient's maxillofacial first region of interest (ROI1) using a patient positioning device;
the method comprises determining features relative to the patient's maxillofacial first region morphology or to the x-ray patient attenuation in the patient's maxillofacial first region based on the reconstructed CBCT slice, the obtaining of operating parameters being based on the determined features;
the determined features relative to the patient's maxillofacial first region morphology include at least one of the width, depth and shape of the dental arch of the patient's maxillofacial first region;
the width of the dental arch of the patient's maxillofacial first region is determined by determining the width between the two ends of the patient's mandibular rami;
the determined features relative to the patient's maxillofacial first region morphology include the relative position of the teeth with respect to the dental arch;
the patient's morphology is determined based on both the width of the maxillofacial first region and the comparison of this width with a predetermined model of different patient's morphologies or predetermined different patient's morphology characteristics;
the patient's morphology is also determined based on the depth of the patient's mandibular rami relative to the position of the incisors;

the predetermined different patient's morphology characteristics include a predetermined set of dental arch shapes including a U shape, a V shape and a square shape;

obtaining operating parameters for an x-ray imaging apparatus that comprises an x-ray source and at least one x-ray sensor based on the reconstructed CBCT slice includes adjusting a trajectory for both ray source and x-ray sensor based on morphological data;

obtaining operating parameters for an x-ray imaging apparatus that comprises an x-ray source and at least one x-ray sensor based on the reconstructed CBCT slice includes adjusting the x-ray dose for the x-ray source based on morphological data;

obtaining operating parameters for an x-ray imaging apparatus that comprises an x-ray source and at least one x-ray sensor based on the reconstructed CBCT slice includes adjusting the x-ray dose for the x-ray source based on a measurement of the x-ray attenuation by the patient's maxillofacial first region bone density on the reconstructed CBCT slice;

obtaining operating parameters for an x-ray imaging apparatus includes one of the following:

selecting a predetermined set of operating parameters;

determining operating parameters based on a predetermined model.

the first x-ray dose does not exceed 20% of the second x-ray dose.

According to still another aspect of the disclosure, there is provided a system for obtaining operating parameters for x-ray imaging a patient's maxillofacial region, comprising:

an x-ray source and at least one x-ray sensor that are configured to move around a patient's maxillofacial first region of interest while irradiating the latter with a slit-shaped x-ray beam formed from a first x-ray dose so as to acquire a first set of data-relative to said patient's maxillofacial first region of interest when the patient is in an occlusion position or bites a patient positioning accessory, said patient's maxillofacial first region of interest including a horizontal plane that passes through the teeth and the bones of the jaw, said first set of data being suitable for generating a CBCT slice, a microprocessor configured to:

reconstruct the CBCT slice comprising the horizontal plane based on the first set of data relative to the patient's maxillofacial first region of interest, obtain operating parameters for an x-ray imaging apparatus based on the reconstructed CBCT slice in view of acquiring a second set of data of a patient's maxillofacial second region using a second x-ray dose, the first x-ray dose being lower than the second x-ray dose.

The microprocessor may also be configured to perform any of the steps, operations, features or aspects of the above method.

According to yet another aspect of the disclosure, there is provided a computer storage medium having instructions stored therein for causing a computer or a microprocessor to perform the method as briefly described above.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 7A-B show different processes to perform step S6 of FIG. 3 algorithm;

FIGS. 8A-E illustrate a process for determining the width and depth of a dental arch;

FIG. 9A illustrates a model for different patient's builds;

FIG. 9B illustrates an example of a panoramic trajectory that has been obtained;

DETAILED DESCRIPTION OF THE EMBODIMENTS

Figure 1:
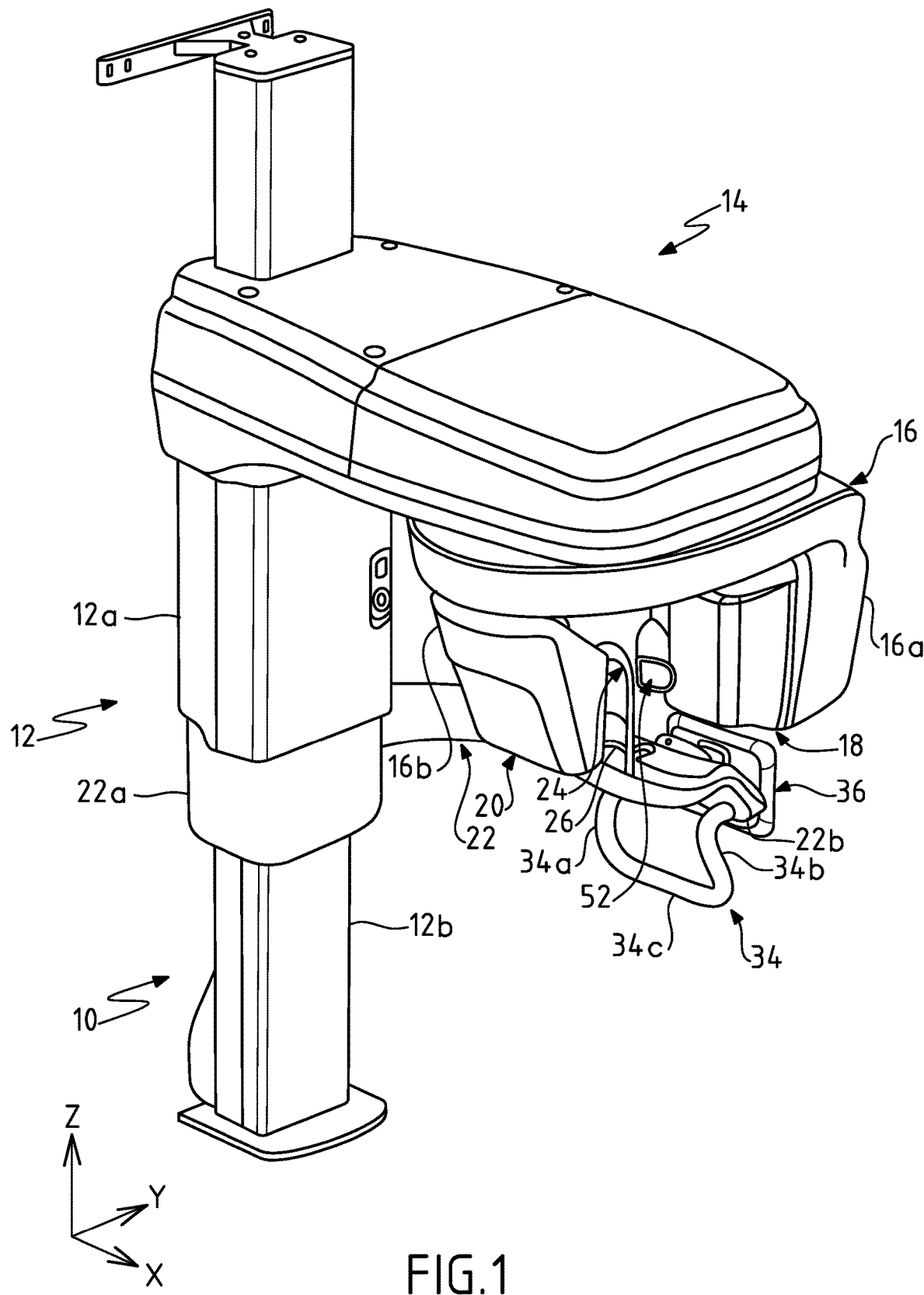
FIG. 1 shows an overall schematic perspective view of an x-ray imaging apparatus according to an embodiment of the invention.

The following is a detailed description of the preferred embodiments, reference being made to the drawings in which the same reference numerals identify the same elements of structure in each of the several figures.

FIG. 1 illustrates an embodiment of an x-ray imaging apparatus, in particular an extra-oral imaging apparatus 10. Apparatus 10 comprises a support structure that includes a support frame 12 which may be a support column.

The support structure also includes a horizontal mount 14 that may be supported or held by the vertical column 12. Horizontal mount 14 extends away from vertical column 12 and may be substantially perpendicular thereto. Horizontal mount 14 can move vertically relative to the vertical column 12.

More particularly, horizontal mount 14 is fixedly mounted on a vertical part 12a that is slidably mounted over a fixed vertical part 12b. For example, an actuator, e.g. of the electric type, located behind the vertical column (not represented in the drawing) can be commanded to drive the horizontal mount 14 into a vertical movement in a controlled manner.

Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation which may be stationary during the operation of the imaging process or may follow one among several predetermined trajectories in accordance with the selected imaging process. A driving known mechanism (not represented in the drawing) for driving the gantry 16 into a given movement is integrated inside horizontal mount 14. By way of example, such driving mechanism includes motors for imparting a first movement in an X, Y plane, e.g. two step-by-step motors, and a motor for imparting a rotational movement about the vertical axis z, e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto. X-ray source 18 includes a conventional collimator (not represented in FIG. 1). The position of the collimator along the vertical axis z and the opening of the slit collimator window may be adjusted so that the collimated x-ray beam irradiates a region of interest of the patient's head or patient's maxillofacial region.

When activated x-ray source 18 emits a collimated x-ray beam which here irradiates an imaging area of a patient's maxillofacial region (or patient's maxillofacial region of interest) before impinging the at least one x-ray sensor 20. In the present embodiment, x-ray source 18 and the at least one x-ray sensor 20 are configured to move around the patient's maxillofacial region along a predetermined trajectory, while irradiating the imaging area of the patient's maxillofacial region. In the present embodiment, the apparatus 10 is used in an x-ray CBCT operating mode for obtaining a 3D CBCT slice as will be seen subsequently. The apparatus 10 may be considered as an x-ray CBCT imaging apparatus to perform volumetric or computerized tomography and obtain 3D images.

However, the apparatus 10 may also function according to one or several other operating modes or imaging processes, such as panoramic, cephalometric, etc.

Figure 3:
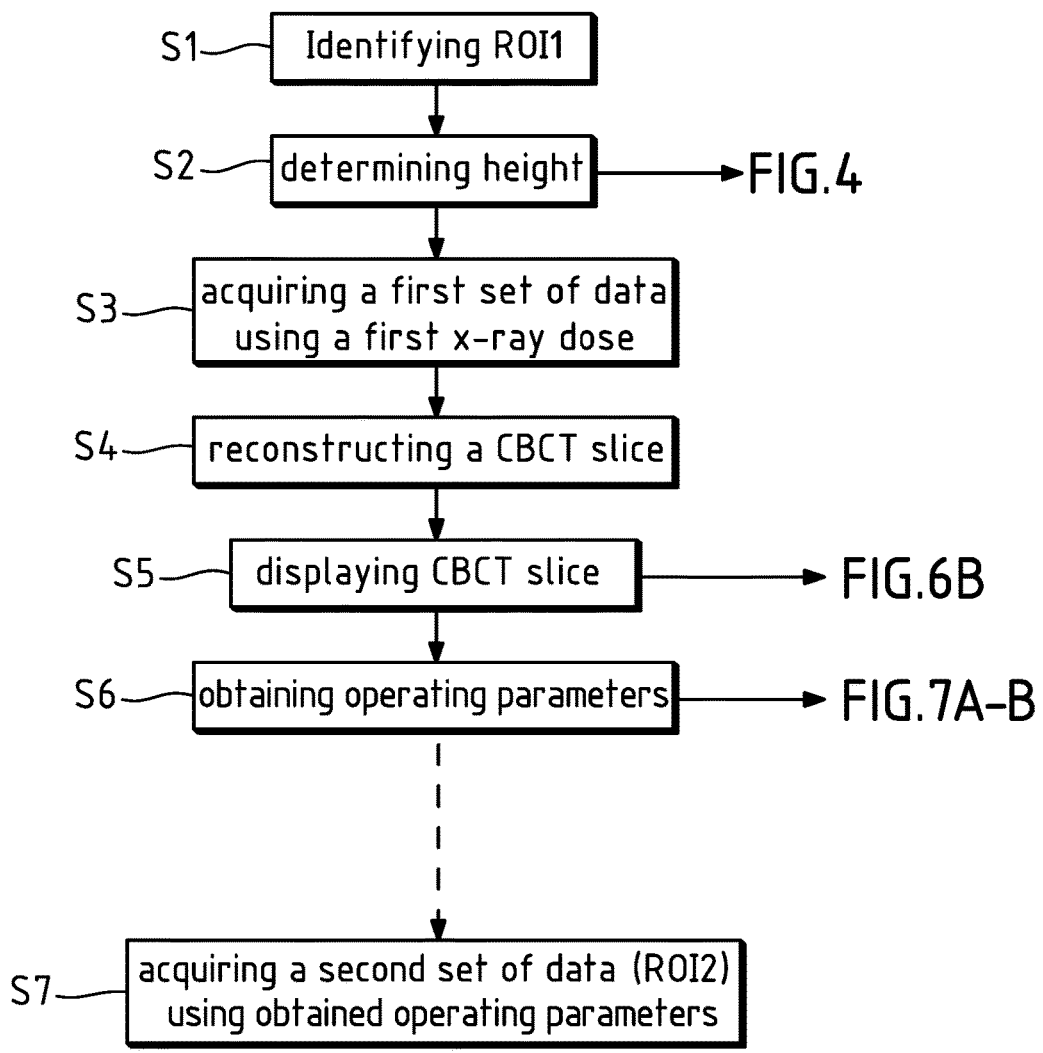
FIG. 3 shows an algorithm of a method according to an embodiment of the invention.

The apparatus 10 is able to operate according to such different operating modes or only some of them based on the operating parameters that will be obtained through the embodiment method of FIG. 3.

In this respect, another sensor or other sensors may be used and the x-ray may be collimated accordingly to irradiate a region of the patient's head as the patient's maxillofacial region (or the whole patient's head) with a specific shape depending on the selected operating mode and choice of the practitioner.

The at least one x-ray sensor 20 includes a sensor that is adapted to one of the operating modes of the apparatus. For instance, the sensor may be adapted to perform a CBCT scan, e.g. a volumetric or computerized sensor (e.g. rectangular, square-shaped), or several sensors of the previous type.

The support structure may also include a patient positioning accessory support member 22 which here is an arm. Arm 22 is connected to the support frame, and more particularly to the vertical column 12. The patient positioning arm 22 is movable relative to the support frame. More particularly, arm 22 can slide along the vertical column 12 so as to move up or down upon command through appropriate actuator(s) e.g. of the electric type. The patient positioning arm 22 extends from an arm support 22a that is slidably mounted relative to the fixed vertical part 12b. The patient positioning arm 22 extends along the apparatus in a direction that is substantially in correspondence with the direction of extension of horizontal mount 14. Patient positioning arm 22 is here arranged sideways relative to the apparatus in a substantial parallel relationship with horizontal mount 14.

Patient positioning arm 22 serves to position the patient in the apparatus at a given location.

Patient positioning arm 22 may include one of several patient positioning accessories generally located at a free end 22b of the arm or proximate thereto. These accessories may also or alternatively be considered as holding systems. These patient positioning accessories allow to position the anatomical structures of the patient's head according to different orientations and to immobilize the patient's head during the examination so as to reduce any possible movement.

There exists one or several types of patient positioning accessories for each type of specific examination to be carried out by the apparatus according to different operating modes. The arm 22 is configured to accommodate each of these patient positioning accessories of different types, generally one at a time.

As illustrated in FIG. 1, one of these patient positioning accessories, noted 24, includes two temporal holding members that extend upwardly from the arm 22 to which they are removably attached. Only one temporal holding member is represented, the other one being hidden by the arm 16b.

The patient positioning accessory 24 may also include a chin rest 26 that extends upwardly from the arm 22 to which it is removably attached. The chin rest 26 is located between the two temporal holding members to position a patient's head for a panoramic examination. A standard bite block may be further added to the chin rest. Alternatively, a Frankfort guide bite block may be used for panoramic examination. Other possible types of patient positioning accessories may be envisaged: a nasal support for conducting a temporal mandible joint examination with open and closed mouth, a bite support for 3D examination (bit type), a frontal support for 3D examination (frontal type), a combination of a bite support and a frontal support, etc. As illustrated in FIG. 1, a handle assembly 34 may be positioned at the free end 22b of the arm, underneath the arm and in a parallel relationship with the arm. This handle assembly 34 includes two vertical separate handle portions 34a, 34b which can be grasped by the patient when undergoing an imaging process so as to remain motionless.

Overall this handle assembly 34 has a U-shape which includes a horizontal base portion 34c and two vertical upwardly-extending branches 34a, 34b that are fixed to the arm 22. Each branch plays the role of a vertical handle portion.

Other handle assemblies may alternatively be used for handling the arm 22.

Patient positioning arm 22 may also support a monitor or display assembly 36 which makes it possible for a practitioner of the apparatus to view images displayed thereon, interact therewith and drive certain functions of the apparatus.

Figure 2:
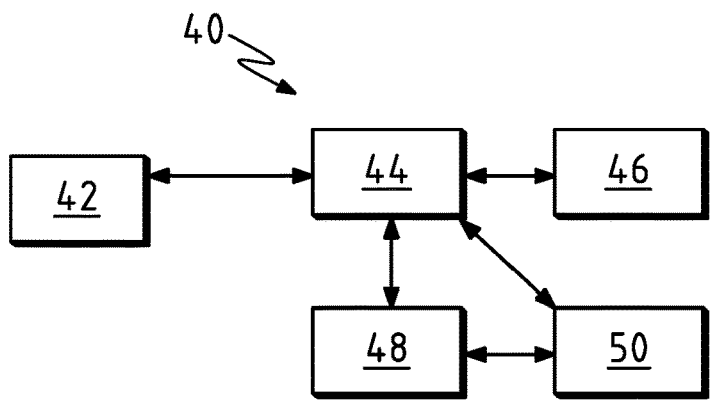
FIG. 2 shows main functional components or assemblies of an x-ray imaging system according to an embodiment of the invention.

FIG. 2 is a schematic view of main functional components or assemblies of a system 40 that will be used in the present embodiment. Some or all of these components or assemblies may be part of the apparatus 10 or not.

In the present embodiment system 40 is located in the apparatus 10.

System 40 comprises an acquisition assembly 42 that includes the x-ray source and x-ray sensor of FIG. 1 apparatus.

System 40 comprises a control assembly 44 that is connected to acquisition assembly 42 and configured to control operation of the latter according to embodiment methods of the invention.

Control assembly 44 may also be used to enable operation of the apparatus 10 and its different components/assemblies in a more conventional manner, in particular to perform CBCT scans and reconstruct 3D volumes (3D x-ray image data) and perform panoramic, cephalometric, etc. data acquisition.

Control assembly 44 includes in particular a microprocessor and possibly one or more storage medium for storing a computer program having instructions for controlling system 40 to practice one or several embodiment methods according to the present invention. When the microprocessor executes the computer program stored in the one or more storage medium the microprocessor is considered as being configured to perform steps or operations of the embodiment method according to the present invention.

An aspect of the present invention is also directed to a computer program product including the one or more storage medium.

The above one or more storage medium may be, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store such a computer program. The stored computer program(s) or other stored computer program(s) may have also instructions for controlling the apparatus 10 to practice more conventional methods such as methods for obtaining a 3D volume.

System 40 may also comprise one or more external storage medium 46 that store, here, different volumes of data reconstructed by the apparatus in the course of x-ray imaging processes, e.g. CBCT imaging processes. The one or more external storage medium 46 may also be of the same type as described above.

The one or more external storage medium 46 may also store the above computer program(s) for controlling system 40 and/or, more generally, for controlling the apparatus 10 instead of the one or more storage medium inherent to control assembly 44.

System 40 further comprises a display assembly 48, here a monitor or screen or several of them, that may correspond to display assembly 36 of FIG. 1. Display assembly 48 is connected to control assembly 44.

Display assembly 48 may display, automatically or on demand, selected images of a patient's maxillofacial region obtained from an x-ray imaging process performed by the apparatus 10.

Display assembly is under control of control assembly 44. System 40 may further comprise a user interface assembly 50 that is connected to display assembly 48 and control assembly 44. User interface assembly 50 allows a user, e.g. a practitioner or technician, to interact with the display assembly 48, and possibly control assembly 44 that executes image processing/algorithms, in order to perform different tasks.

The user interface assembly 50 may include one or more interaction devices connected to display assembly 48, such as, but not limited to, a pointing device, e.g. a computer mouse joystick, a stylet, a keypad, a touchpad etc.

Other types of interaction devices or tools (user interface tools) may alternatively, or in addition, be used: a touch screen, tool icons displayed or that may be displayed on command on the screen, etc.

Assemblies 44, 46, 48 and 50 may be located in whole or in part in the arm 22 of apparatus 10 or remotely-located relative to the apparatus (e.g. in the same room or in a separate room or in another place). If control assembly 44 is not located in the apparatus 10, another control assembly may be present in the apparatus so as to control the acquisition assembly 42 and, in a general manner, the operation of the apparatus. However, the whole description applies equally whatever the location of the assemblies.

The above also applies if assemblies 42, 44, 46, 48 and 50 pertain to another type of x-ray imaging apparatus.

An embodiment method according to the invention will now be described with reference to FIG. 3 which depicts an algorithm of the corresponding computer program(s). This algorithm makes reference to other algorithms that are illustrated on other figures and that may be part of the same computer program or correspond to other computer programs.

For its operation the embodiment method makes use of functional components or assemblies that can be those described above in connection with FIG. 1 apparatus 10. Alternatively, the functional components or assemblies necessary to perform the method may be those of another x-ray imaging apparatus and may be in accordance with the configuration of FIG. 2 (all the components of FIG. 2 may however not be present).

A patient is first positioned in the working space of apparatus 10 between the x-ray source 18 and x-ray sensor 20 of acquisition assembly 42, e.g. in a sitting position. The method starts with an identification step S1 for identifying a patient's maxillofacial first region of interest denoted ROI1. The practitioner identifies ROI1 based on predetermined criteria such as the type of examination to be carried out on a second region of interest ROI2 of the patient's maxillofacial region, the second region of interest ROI2 itself, etc. For example, ROI1 may include the upper and lower jaws, part of both jaws, only one jaw, part of a single jaw etc. depending on the interest of the practitioner. The latter may be particularly interested by the two upwardly extending portions or rami of the mandibular jaw or mandible, in particular by the anterior and/or posterior end of each ramus, etc.

Figure 4A:
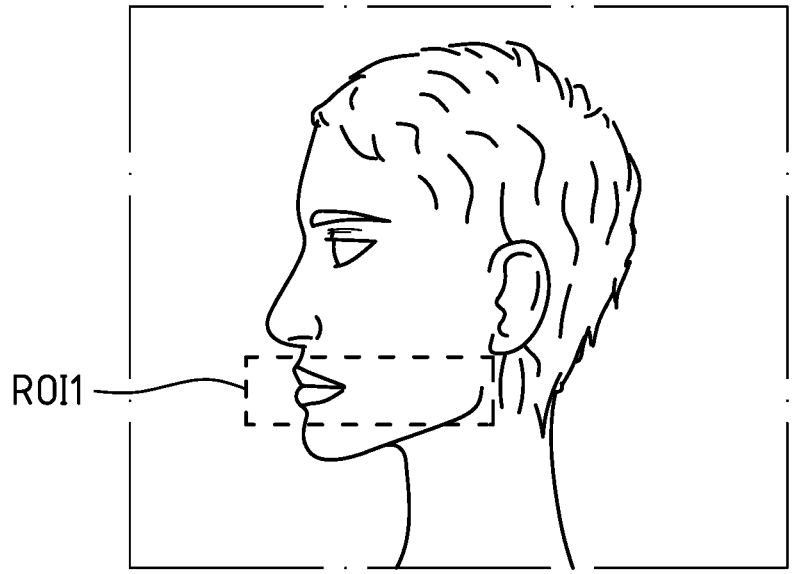
FIG. 4A illustrate the FIG. 3 step S1.

FIG. 4A illustrates ROI1 that has been identified by the practitioner on a lateral view of the patient's maxillofacial region. To be noted that the result of this step may be viewed on the display assembly of FIG. 2 as illustrated on FIG. 4A. The method further comprises a height determination step S2. For the performance of this step the patient may be in an occlusion position, i.e. his/her upper and lower jaws have to be in contact with each other.

Alternatively, the patient may bite in a patient positioning member or accessory and his/her teeth are then spaced from a few millimeters. Such a patient positioning member or accessory may be attached to the arm 22 in a releasable manner. Such a patient positioning member or accessory may be a bite block, e.g. a Frankfurt guide bite block used for panoramic examination, a standard bite block, a bitten 3D support etc.

In the present embodiment the patient is in an occlusion position and his/her head may be maintained in position through a chin rest, a frontal support including a chin rest etc. The identified ROI1 includes the occlusal plane.

The aim of this step is to determine a height of a horizontal plane within ROI1. This height will be used next for a first x-ray data acquisition. The horizontal plane has to pass through the teeth and the bones of the jaw so that useful morphological data may then be extracted during next steps of the method. Preferentially, the horizontal plane has to pass through the teeth roots and the bones of the mandibular jaw. In another embodiment, the horizontal plane has to pass through the teeth roots and the bones of the upper jaw.

This horizontal plane may be a median plane of ROI1 or another plane within ROI1. For the performance of this step the patient may also be positioned so that his/her Camper plane or Frankfurt plane be horizontal.

Figure 4B:
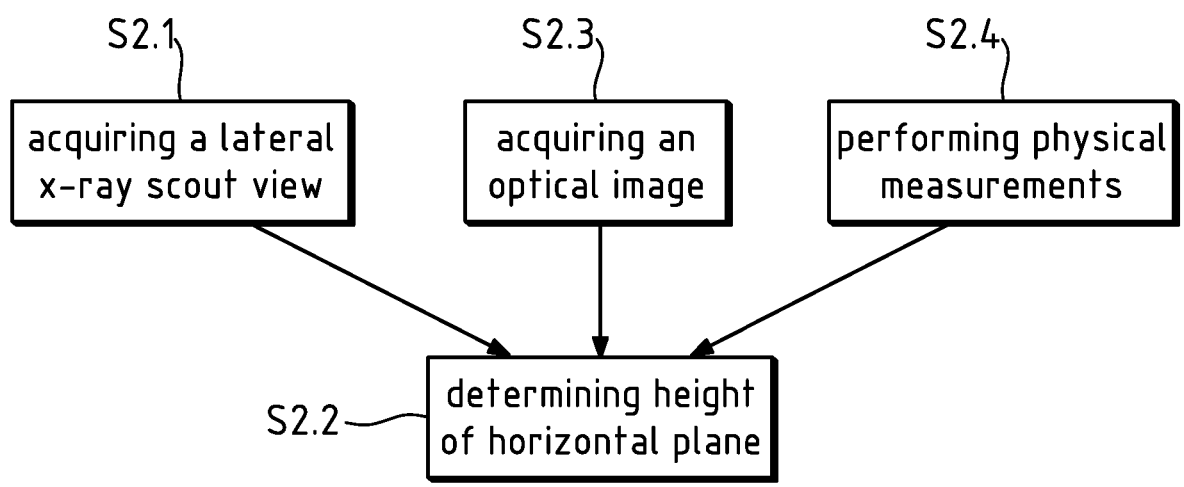
FIG. 4B shows different processes to perform the FIG. 3 step S2.

FIG. 4B shows different ways for determining the height of the horizontal plane. A first way is to acquire an x-ray lateral scout view of the patient (step S2.1) through the acquisition assembly 42 operated under the control of control assembly 44 of FIG. 2.

Figure 5A:
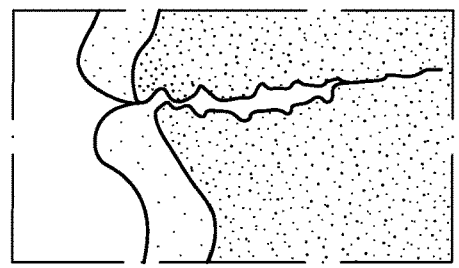
FIG. 5A-D illustrate the first process of FIG. 4.

FIG. 5A illustrates an x-ray lateral scout view (original image) of the patient that has been acquired in a conventional manner. Such a view may provide information on the upper and lower jaws and ROI1 that has been previously identified by the practitioner. However, depending on the scout view, information about only one jaw may be available. To be noted that in the present embodiment, the scout view has been chosen as corresponding to the ROI1 identified in FIG. 4A. The position of the scout view relative to the patient's jaw may have been previously determined based on predetermined mean values.

In a variant embodiment, if the scout view does not correspond to the ROI1 that has been previously identified (ex: that of FIG. 4A in this example embodiment), the scout view may further be cropped with respect to patients' mean morphological data so as to obtain the desired ROI.

Figure 5B:
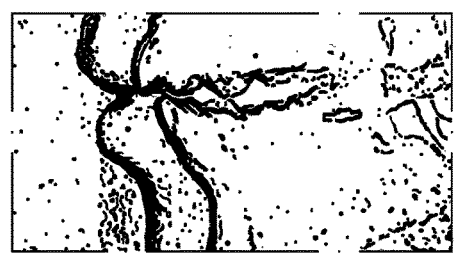
Figure 5C:
Figure 5D:
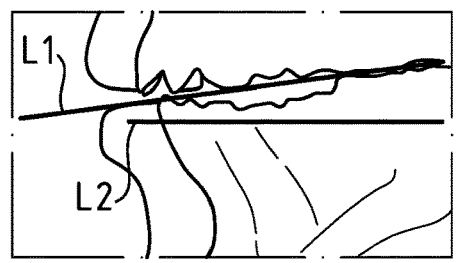

FIGS. 5B-D illustrate a few steps of the process based on the acquired x-ray lateral scout view of FIG. 5A to determine the horizontal plane of interest within ROI1 and its height.

These steps are conventional image processing steps comprising applying a correction factor to the grey pixel values of FIG. 5A, computing a gradient on the corrected pixel values thus obtained and binarizing the latter through a predetermined threshold (FIGS. 5B-C).

The occlusal plane is then determined through conventional steps, e.g. using a hough transform to find a set of crossing straight lines and identifying the mean of these crossing straight lines that is represented in FIG. 5D by a first line L1. In the present embodiment line L1 passes by the apex of the lower incisor. The mean size (height) of an incisor for a given patient (adult, child etc.) is known and it is therefore an easy task to geometrically position along the height (z-axis) the horizontal plane of ROI1 in FIG. 5D. The position of this horizontal plane that passes here through the teeth roots and the bones of the mandibular jaw is determined by computation (e.g. after it has been selected by the practitioner once ROI1 has been identified) or directly selected by the practitioner on FIG. 5D.

In the present embodiment, a second line L2 that is horizontal and spaced from line L1, here below line L1 (e.g. a few millimeters below), has been illustrated. This second line L2 represents a projection of this horizontal plane in the plane of FIG. 5D. Next, at step S2.2 the height of L2 is determined in a conventional manner based on the known position of the scout view relative to the used patient's positioning accessory and the known position of the latter relative to the x-ray apparatus, in particular the arm 22. To be noted that the position of the x-ray source relative to the arm is also known.

In a variant embodiment, the horizontal plane to be aimed at for acquiring a first set of data and its height may be determined without passing by the determination of the occlusal plane.

Figure 5E:
FIG. 5E illustrates the position of a horizontal plane L3 for acquiring the first set of data.

FIG. 5E illustrates an example of a position of a horizontal plane L3 that can be determined according to such a variant embodiment.

Two other ways for determining the height of a horizontal plane are illustrated on FIG. 4B.

A second way (step S2.3) makes provision for acquiring at least one optical image of the patient (in the occlusal position) comprising the patient's maxillofacial first region of interest ROI1 including landmarks. The at least one image is more particularly a facial image taken by a camera and the landmarks may be of the anatomical type (ex: the corners of the mouth) or landmarks that have been added on the patient's face. The camera may be positioned on the apparatus 10, e.g. on the arm 22 or independent from the apparatus. On FIG. 1 an example of a camera 52 is located next to x-ray source 18. Another location for a camera may alternatively be selected.

Alternatively, a lateral optical image of the patient may be convenient instead of the facial one.

The landmark or landmarks are representative of a geometrical position that is known or can be easily known by computation relative to the teeth roots.

As a consequence, the height of a horizontal plane passing by the teeth roots and the bones of the mandibular jaw that can be used for the first x-ray data acquisition can therefore be determined by computation based on the position of the landmark or landmarks (step S2.2).

A third way (step S2.4) makes provision for performing physical measurements on the patient (in the occlusal position), more particularly on the patient's maxillofacial first region of interest (ROI1), using a patient positioning device or accessory.

A patient positioning accessory attached to the arm 22 of FIG. 1 may be used, e.g. a bite block or the like. The bite block is attached to the arm in a fixed position and the height of the bite block relative to the arm is known or can be measured. The mean size (height) of teeth for a given patient (adult, child etc.) are also known, which makes it possible to situate the position of teeth roots and therefore their position relative to the teeth extremities, i.e. the bite block.

Consequently, the height or position of the horizontal plane of ROI1 relative to the arm may be determined by measurements and/or computation based on the above. Alternatively, a sensor located in the bite block or the like may provide appropriate measurement data and the height or position of the horizontal plane relative to the arm may next be determined therefrom.

Then, the height of a horizontal plane that can be used for the first x-ray data acquisition can be determined (step S2.2). This prior determination phase aims at determining the height at which the first set of data relating to ROI1 will be acquired.

Once the height of the horizontal plane has been determined, the apparatus 10 is set accordingly by control assembly 44 in a configuration that enables acquisition of the first set of data as provided by step S3 of FIG. 3. The first set of data may correspond to the whole ROI1 or to a selected portion thereof.

Two ways are used for setting the apparatus in the acquisition configuration:
firstly, the set of x-ray source and x-ray sensor is commanded by control assembly 44 to be moved to the determined height so that the x-ray source be at the appropriate height for the acquisition; this arrangement makes it possible to reduce the x-ray dose easily;
secondly, the x-ray source remains at the same altitude and the x-ray collimator is moved so as to orientate the x-ray beam upwardly towards the determined height of the plane.

For this first data acquisition the patient remains in the occlusal position or bites a bite support as provided for at previous step S2. The patient may also be positioned so that his/her Camper plane or Frankfurt plane be horizontal as for step S2.

For this first data acquisition the apparatus 10 is in an operating CBCT mode under the control of control assembly 44.

According to this mode the x-ray collimator opening is adjusted as a slit-shaped collimator window so as to produce a slit shaped x-ray beam focused on the patient's maxillofacial first region of interest (ROI1) including the horizontal plane. Although the x-ray beam has been described as focused on the whole ROI1 it is to be understood here and in the remainder of the description that the x-ray beam may be focused on a portion of ROI1 only (ex: a slice) including the horizontal plane. This slit shape for the beam is adjusted so as to cover widthwise the whole dental arch with the two ramus and a thin volume in height. The horizontal plane of ROI1 is aimed at thanks to the adjustment in the collimator position and the collimator window opening.

Figure 6A:
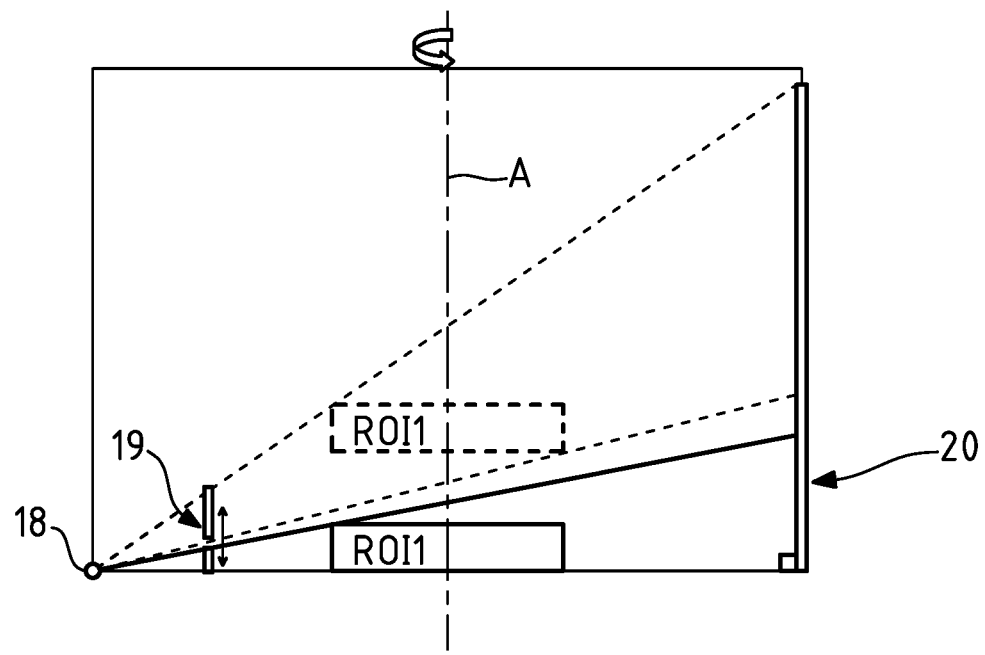
FIG. 6A illustrates relative positions between the ROI1 and the x-ray source.

FIG. 6A illustrates two different relative positions between the x-ray source 18 and ROI1 (ROI1 could alternatively be replaced by a portion thereof and the remainder of the description applies equally) with different openings for the x-ray collimator 19. As represented, the x-ray source 18 is in alignment with the lower end of the sensor 20 and the axis of rotation A of the set composed of the source and the sensor has also been illustrated. In order to capture and reconstruct a CBCT slice, the opening of the collimator in the vertical direction depends on the position of the collimator relative to the source-sensor alignment. The smallest opening is obtained when the source-sensor axis passes by the collimator. In other words, the median plane of the collimated x-ray beam is adjusted so as to obtain for the collimator the smallest opening that is necessary for the slice reconstruction.

Preferentially, the source-sensor axis passes by the basis of the collimator window and the lower edge or boundary of ROI1.

The x-ray source is operated with a first x-ray dose that may be qualified as a low dose with respect to the x-ray dose that will be used for a subsequent second x-ray data acquisition. The first x-ray dose is selected so as to minimize x-ray exposure for the patient. The x-ray dose depends on the volume of data to be acquired. The volume is as small as possible and does not need high resolution for first x-ray data acquisition since the useful information that is needed for the remainder of the method lies in the morphological characteristics or data of the patient maxillofacial region (location of the teeth, morphology of the teeth, characteristic dimensions, etc.). Such information does not require many details in the acquired data.

Typically, the first x-ray dose does not exceed 20% of the second dose that will be used for a subsequent second data acquisition.

Preferentially, the first x-ray dose does not exceed 10% of the second dose and, more preferentially, does not exceed 5% of the second dose.

For example, a first x-ray dose may be in the order of 4 µSv for generating a CBCT slice.

Reverting to FIG. 3, the third step S3 for acquiring a first set of data (3D volume) is based on the above settings and adjustments. This first acquisition may be viewed as a "pre-shoot" for extracting useful information that will be used for a subsequent "shoot". The exposure time for this pre-shoot is rather low, e.g. in the order of 5 s.

Next step S4 is a reconstruction step for reconstructing a CBCT slice based on the acquired first set of data using conventional CBCT data processing techniques (e.g. the FDK algorithm).

The reconstructed CBCT slice comprises the horizontal plane of ROI1 and is based on the acquired first set of data relative to the patient's maxillofacial first region of interest (ROI1).

As an example of the low resolution in the first acquired data a voxel size around 500 µm in the reconstructed CBCT slice can be obtained. For example, the thickness or height of the slice lies between 10 and 30 voxels, thereby corresponding to a range between 1 and 15 mm. A range between 1 and 5 mm may preferentially be selected. The reconstructed CBCT slice may take the shape of a cylinder (another shape may be convenient) with a diameter lying between 120 mm (for small skull dimensions) and 160 mm. Such a diameter enables acquisition of the whole dental arch.

Figure 6B:
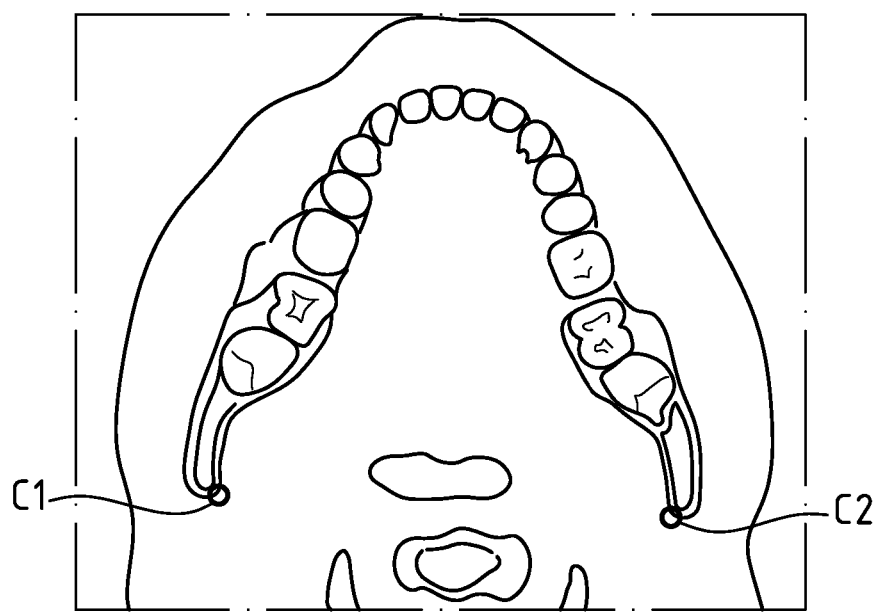
FIG. 6B shows an axial view of the reconstructed CBCT slice.

Optionally, the method comprises a further display step S5 for displaying an axial slice of the reconstructed 3D volume as illustrated on FIG. 6B. FIG. 6B shows the dental arch and in particular the two rami and incisors. This step makes it possible to view the ROI1 and then control the shape of the dental arch. The points used in the measurements performed on the dental arch may also be viewed.

Next step S6 makes provision for obtaining operating parameters for an x-ray imaging apparatus based on the reconstructed CBCT slice in view of acquiring a second set of data of a patient's maxillofacial second region of interest (ROI2) using a second x-ray dose.

This step is further detailed in the algorithms of FIGS. 7A and 7B.

FIG. 7A comprises a step S6.1 for determining features relative to the patient's maxillofacial first region of interest morphology based on the reconstructed CBCT slice and, in particular, information inherent thereto.

The features relative to the patient's maxillofacial first region of interest morphology include at least one of the width, depth, shape of the dental arch of the patient's maxillofacial first region of interest and the relative position of the teeth with respect to the dental arch.

In the present embodiment the width and depth of the dental arch are determined based on the reconstructed CBCT slice. The width and depth of the dental arch are determined as illustrated on FIGS. 8A-E.

FIG. 8A illustrates an axial view of the reconstructed slice as in FIG. 6B.

FIG. 8B is obtained from FIG. 8A by applying a threshold on the gray value of the data and removing the spine area.

FIG. 8C represents the left half of the thresholded image of FIG. 8B. The process starts from the bottom of the image to find the first line with white pixel therein, which corresponds to the presence of bone. This corresponds to the Y value of the dental arch limit. The same process takes place on the right half image.

Then the lines of the left half image around the detected Y value are considered. The process starts from the left part of the left half image (outside of the skull) to find the first column with white pixels therein, which corresponds to the presence of bone. This corresponds to the X value of the dental arch limit as illustrated on FIG. 8D. The same process takes place on the right half image.

FIG. 8E illustrates on the original image of the reconstructed slice as in FIGS. 6B and 8A the detected limits illustrated by two separate circles C1 and C2.

The width of the dental arch may be determined by determining the width between the two ends of the patient's mandibular rami that are illustrated by the two separate circles C1 and C2 respectively. In particular, the ends of interest here are the posterior ends of the rami. For another purpose, the anterior ends of the rami may be of interest. This width is determined by computation from the reconstructed slice data stored in memory.

The depth of the dental arch is determined by computation from the reconstructed slice data stored in memory between the Y position of the incisors and the Y position of one of the posterior ends of the patient's mandibular rami.

The position of the teeth relative to the dental arch may be of help to obtain a source-sensor trajectory with great accuracy. This is of interest for example for panoramic examination where the trajectory has to be perpendicular to the teeth and therefore characterized in order to avoid that part of the panoramic image be blurred. Obtaining a blurred image would require a complete entire acquisition, which would increase the x-ray dose for the patient.

FIG. 7A comprises a second step S6.2 for determining a patient's build based on at least some of the above determined features, here the width and depth of the patient's dental arch.

This step may be performed in accordance with two different processes.

In a first process S6.2.1 the patient's build is determined from a predetermined model of different patient's morphologies or builds using the determined values of the width and depth. Such a model has been previously conceived from a number of measurement and empirical data performed on a plurality of patients.

FIG. 9A illustrates such a model with a continuum of values and several domains or areas defining several patient's morphologies or builds from top to bottom: XS (extra Small), S (Small), M (Medium) and L (Large).

The point P identified by the determined values of the width (half-width) and depth corresponds to the arch limit that has been determined with reference to FIGS. 8A-E. Here the point P is located in the M domain. The build of the patient will therefore be classified as Medium.

In a second alternative process S6.2.2 the patient's build is determined from a set of predetermined characteristics using the determined values of the width and depth. FIG. 7A comprises a further step S6.3 for determining a shape of the patient's dental arch based on at least some of the above determined features, here the width and depth of the patient's dental arch.

This step may be performed in accordance with two different processes.

In a first process S6.3.1 the dental arch shape is determined from a predetermined model of different patient's morphologies or dental arch shapes using the determined values of the width and depth. Such a model has been previously conceived from a number of measurement and empirical data performed on a plurality of patients and includes a continuum of values.

To be noted that use of a model for dental arches may lead to greater accuracy for the source-sensor trajectory, which is of interest for panoramic examination as already explained above, to avoid that part of the panoramic image be bluffed.

In a second alternative process S6.3.2 the patient's dental arch shape is determined from a set of predetermined dental arches including a U shape, a V shape and a square shape, using the determined values of the width and depth.

In a still alternative process, the shape of the dental arch is measured from the reconstructed slice data stored in memory.

To be noted that steps S6.2 and S6.3 may be timely inverted: step S6.3 may be performed before step S6.2.

Twelve combinations can therefore be obtained for a patient given the 4 builds and the 3 dental arch shapes.

Each combination may be characterized by appropriate operating parameters to be used such as the x-ray dose to be used, the exposure time to x-rays, the trajectory to be followed by the x-ray source and x-ray sensor during the imaging process (panoramic, etc.), etc.

Once these characteristics of the patient's morphology (builds and dental arches) have been determined from the reconstructed CBCT slice, operating parameters may then be obtained in accordance therewith.

Next step S6.4 provides for obtaining or adjustment of operating parameters based on the previous determined features or characteristics.

Practically, the following parameters linked with the x-ray dose may be adjusted:
   the peak voltage (unity: kVp) that is currently applied to the x-ray tube of the x-ray source determines the highest energy of x-ray photon;
   the electric current (unity: mA) that is currently applied to the x-ray tube results in the generation of electrons inside the x-ray tube: an increase in current results in a higher generation of electrons, which increases the quantity of radiation and therefore the quantity of photons reaching the sensor and hence the x-ray density;
   the time factor (unity: s) is representative of the electron generation duration within the x-ray tube and, therefore, indicates the duration of application of the current intensity.

Other operating parameters including the trajectory of the source-sensor set may also be adjusted. For the panoramic examination, the trajectory has to be as accurate as possible to avoid a blurred image as seen above.

FIG. 9B represents an example of a panoramic trajectory for a large patient's build that can be obtained through the performance of the method embodiment, in particular based on the position of the teeth relative to the patient's dental arch.

The shape of the dental arch is marked a1.

Different successive positions at different instants of the x-ray source-x-ray segment are marked a2 for half the trajectory only (on the right part of the trajectory only). The trajectory of the rotation center of the x-ray source-x-ray sensor set is marked a3. The two curves marked a4 and a5 define therebetween the width or thickness of the focal trough which depends on the trajectory.

The line marked a6 represents the furthest position of the x-ray source-x-ray sensor set and is dependent on the width and depth of the patient's dental arch, and therefore on the patient's build. Thus, the lines illustrated in FIG. 9A correspond each to the a6 line on FIG. 9B for a different patient's build.

It is to be noted that the above models and predetermined features, characteristics, values, dental arch shapes etc. have been discussed in relation with the mandibular jaw. They are adapted to reference points that have been selected on the mandible (body and rami) and to the height of the horizontal plane. The above discussion also applies to the upper jaw. However, the models and predetermined features, characteristics, values, dental arch shapes etc. differ for the upper jaw.

The above operating parameters may easily be obtained either by selecting operating parameters from a set of predetermined operating parameters or by determining operating parameters based on a predetermined model of operating parameters. In the present embodiment, the above described method makes it possible to determine patient's morphology features or characteristics directly from a first set of data acquired on the patient, with a rather low x-ray dose compared with the x-ray dose to be used for subsequent x-ray data acquisition. The thus determined patient's morphology features or characteristics are therefore more reliable and accurate data than mean data based on average measurements previously performed on a plurality of patients. The method then allows to obtain operating parameters based on the thus reliable and accurate determined patient's morphology features or characteristics. The obtained/adjusted parameters are therefore more adapted/optimized to the patient than in the past, which leads to higher quality image and less x-ray dose for the patient in the subsequent x-ray data acquisition using these parameters.

In a further embodiment, the above described method is performed automatically (i.e. all the steps of the method are performed by a computer or processor-based apparatus, except maybe the identification of the ROI1), which makes it possible to obtain operating parameters without the practitioner interference. In addition to the above mentioned advantages, the method is therefore much less prone to human errors, and therefore much more reliable.

For instance, the selection of the patient build and dental arch among predefined builds and arches available in the x-ray apparatus is not an easy task for the practitioner. If an error occurs through this selection the operating or acquisition parameters may not be adapted to the patient. Then, for instance, the x-ray dose received by the patient may be too high relative to the dose that would have been necessary or, alternatively, too low, which will require for the patient to be exposed to another higher x-ray dose. This represents a simplified method for the practitioner which may avoid interpretation errors that could be made by the practitioner.

FIG. 7B illustrates another embodiment method for obtaining operating parameters through measuring features relating to x-ray attenuation by the patient's maxillofacial first region of interest bone density based on the reconstructed CBCT slice of step S4 in FIG. 3.

The first step S6.10 is a step for determining features relating to x-ray patient's attenuation from the reconstructed CBCT slice.

A possible feature relating to x-ray patient's attenuation is Contrast to Noise Ratio (CNR). Such a feature takes into account the level of contrast obtained for the propagation of x-rays through the irradiated zone (patient's attenuation) and the air as well as the noise level with the first x-ray dose The reconstructed slice makes it possible to directly obtain the "patient's attenuation" on the x-ray sensor without involving the thickness of the irradiated zone.

Figure 10:
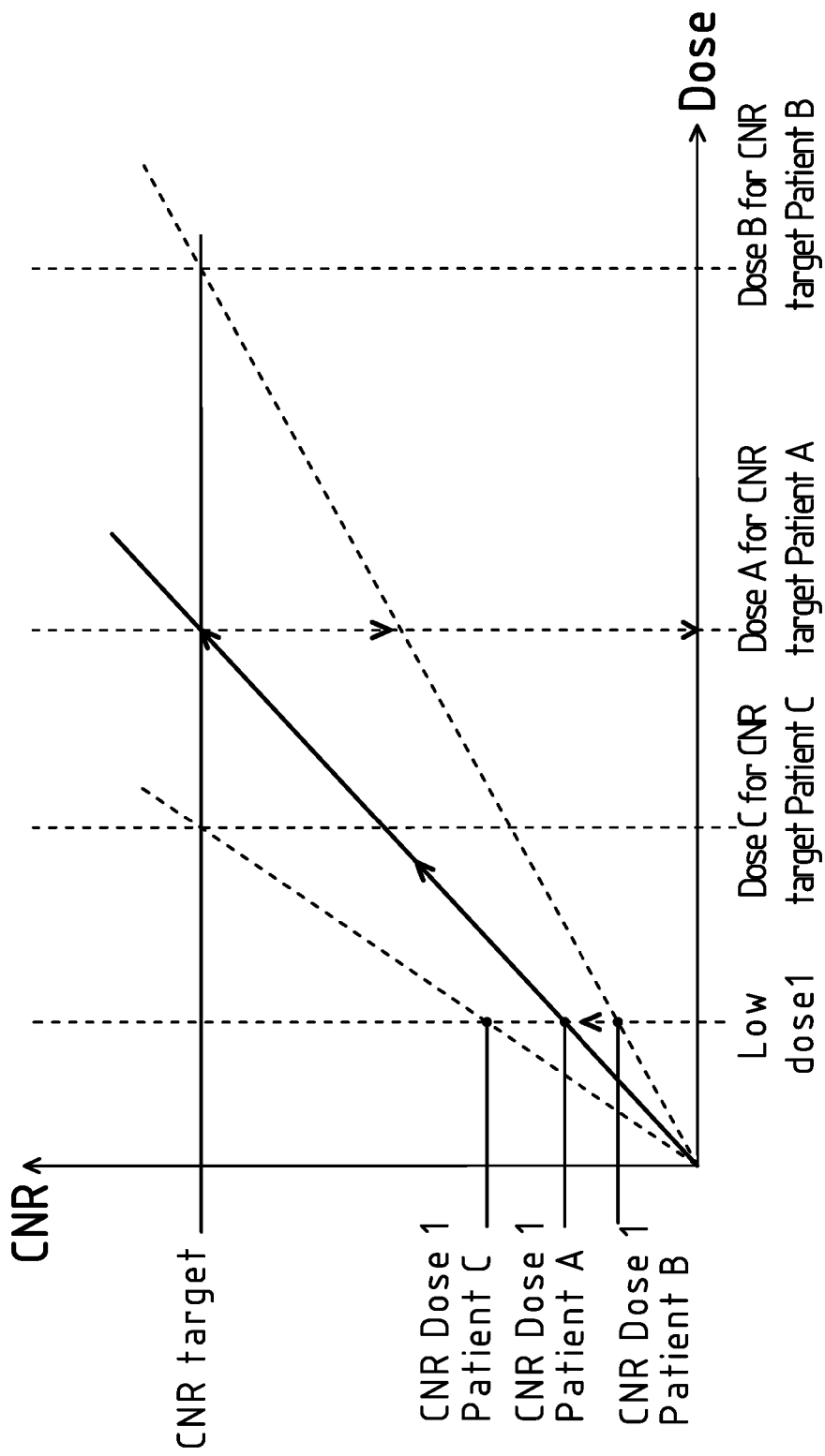
FIG. 10 is a diagram of CNR values according to x-ray doses.

FIG. 10 is a diagram showing CNR values as a function of x-ray dose. This diagram is established based on measurements performed on a plurality of patients and represents of model of predetermined CNR values-x-ray doses.

For example, with a first low dose 1 a first CNT has been achieved (CNR Dose 1 Patient A) with the first x-ray data acquisition and the reconstructed slice. Following one of the straight lines passing through the origin and the achieved CNR, and given a CNR target to be achieved for the subsequent image to be acquired, this leads to a given x-ray dose: Dose A for CNR target Patient A (see the indication provided by the arrows).

This therefore makes it possible to obtain operating parameters as the x-ray dose accordingly (step S6.11).

As already explained above, the following practical operating parameters linked with the x-ray dose may be adjusted: the peak voltage (unity: kVp), the electric current (unity: mA) and the time factor (unity: s).

Other operating parameters including the trajectory of the source-sensor set may also be adjusted.

The above operating parameters may easily be obtained based on the determined patient's x-ray attenuation either by selecting operating parameters from a set of predetermined operating parameters or by determining operating parameters based on a predetermined model of operating parameters.

The operating or acquisition parameters that have been obtained at step S6 (see above description of FIGS. 7A-B) may be used in the course of a subsequent step S7 for acquiring a second set of data of a patient's maxillofacial second region of interest (ROI2) using a second x-ray dose. This acquisition step may be separate in time from the first steps S1 to S6, e.g. by several hours, days, months, etc. The obtained operating or acquisition parameters can then be stored while waiting for being used. To be noted that there is no need for the patient to occupy the same position as for the first data acquisition. However, for the sake of simplicity, the patient remains in the same position. For a panoramic examination the same patient's position is preferably used. The obtained operating or acquisition parameters may be used to adjust an x-ray imaging apparatus (not necessary the apparatus 10) in view of acquiring CBCT, panoramic, cephalometric, etc. data relative to the patient.

The x-ray dose that is used for this second data acquisition is higher than the first x-ray dose for generating a slice: the first x-ray dose is less than or equal to 20% of the second x-ray dose.

By way of example, the first x-ray dose is 4 μSv and the second x-ray dose is:
    between 20 and 30 μSv for a panoramic examination;
    200 μSv for a 3D examination with a large field of view (17×13 cm);
    20 μSv for a 3D examination with a 5×5 cm field of view.

By way of example, the duration of the exposure to x-ray for the second data acquisition is:
    between 10 and 20 s for a panoramic examination;
    between 5 and 20 s for a 3D examination, compared with an approximately 5 s duration for the first data acquisition.

By way of example, the resolution of the image(s) obtained through the second data acquisition is defined by:
    a 100 μm pixel size for a panoramic examination;
    a 100 μm voxel size for a 3D examination,
compared with a 500 μm voxel size for the first data acquisition.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for obtaining operating parameters for x-ray imaging a patient's maxillofacial region, the method comprising the steps of:
    identifying a patient's maxillofacial first region of interest (ROI1);

determining a height of a horizontal plane of said patient's maxillofacial first region of interest (ROI1) when the patient is in an occlusion position or bites a patient positioning accessory, said horizontal plane passing through the teeth and the bones of the jaw;

acquiring through a slit-shaped collimator window a first set of data relative to said patient's maxillofacial first region of interest (ROI1) including the horizontal plane using x-ray CBCT imaging and a first x-ray dose, said first set of data comprising a first set of x-ray images including the horizontal plane obtained at different angular positions relative to the patient's maxillofacial first region of interest (ROI1) and suitable for generating a CBCT slice;

reconstructing the CBCT slice comprising the horizontal plane based on the first set of data relative to the patient's maxillofacial first region of interest (ROI1); and obtaining operating parameters for an x-ray imaging apparatus based on the reconstructed CBCT slice in view of acquiring a second set of data of a patient's maxillofacial second region of interest (ROI2) using a second x-ray dose, the first x-ray dose being lower than the second x-ray dose.

2. The method of claim 1, wherein determining a height of the horizontal plane of the patient comprises beforehand one of the following:

acquiring a lateral x-ray scout view comprising the patient's maxillofacial first region of interest (ROI1); or acquiring an optical image comprising the patient's maxillofacial first region of interest (ROI1) including landmarks; or performing physical measurements on the patient's maxillofacial first region of interest (ROI1) using a patient positioning device.

3. The method of claim 1, wherein the method further comprises a step of determining features relative to the patient's maxillofacial first region morphology or to the x-ray patient attenuation in the patient's maxillofacial first region based on the reconstructed CBCT slice, wherein obtaining operating parameters is based at least in part on the determined features.

4. The method of claim 3, wherein the determined features relative to the patient's maxillofacial first region morphology include at least one of the width, depth, or shape of the dental arch of the patient's maxillofacial first region.

5. The method of claim 4, wherein the width of the dental arch of the patient's maxillofacial first region is determined by determining the width between the two ends of the patient's mandibular rami.

6. The method of claim 3, wherein the determined features relative to the patient's maxillofacial first region morphology include the relative position of the teeth with respect to the dental arch of the patient's maxillofacial first region.

7. The method of claim 4, wherein the patient's maxillofacial first region morphology is determined based on both the width of the maxillofacial first region and a comparison of the width with a predetermined model of a different patient's morphologies or a predetermined different patient's morphology characteristics.

8. The method of claim 7, wherein the patient's maxillofacial first region morphology is also determined based on the depth of the patient's mandibular rami relative to the position of the incisors.

9. The method of claim 7, wherein the predetermined different patient's morphology characteristics include a predetermined set of dental arch shapes including a U shape, a V shape and a square shape.

10. The method of claim 1, wherein obtaining operating parameters for an x-ray imaging apparatus that comprises an x-ray source and at least one x-ray sensor based on the reconstructed CBCT slice includes adjusting a trajectory for both the x-ray source and the x-ray sensor based on morphological data.

11. The method of claim 1, wherein obtaining operating parameters for an x-ray imaging apparatus that comprises an x-ray source and at least one x-ray sensor based on the reconstructed CBCT slice includes adjusting the x-ray dose for the x-ray source based on morphological data.

12. The method of claim 1, wherein obtaining operating parameters for an x-ray imaging apparatus that comprises an x-ray source and at least one x-ray sensor based on the reconstructed CBCT slice includes adjusting the x-ray dose for the x-ray source based on a measurement of the x-ray attenuation by the patient's maxillofacial first region bone density on the reconstructed CBCT slice.

13. The method of claim 1, wherein obtaining operating parameters for an x-ray imaging apparatus includes one of the following:

selecting a predetermined set of operating parameters; or determining operating parameters based on a predetermined model.

14. The method of claim 1, wherein the first x-ray dose does not exceed 20% of the second x-ray dose.

15. A computer storage medium having instructions stored therein for causing a computer or a microprocessor to perform the method of claim 1.

16. The method of claim 1, wherein the method further comprises a step of determining a morphology characteristic of the patient's maxillofacial first region of interest (ROI1) based on the reconstructed CBCT slice, wherein the obtained operating parameters for said acquiring the second set of data of the patient's maxillofacial second region of interest (ROI2) using the second x-ray dose are based at least in part on the determined morphology characteristic.

17. The method of claim 1, further comprising the steps of:

acquiring the second set of data that comprises a second set of x-ray images obtained at different angular positions including the patient's maxillofacial second region of interest (ROI2) using the second x-ray dose; and reconstructing a 3D CBCT image including the defined second region of interest (ROI2); based on the acquired second set of data, wherein the 3D CBCT image has a higher resolution than the CBCT slice.

18. The method of claim 1, wherein the obtained operating parameters for the x-ray CBCT imaging apparatus for acquiring the second set of data of the patient's maxillofacial second region of interest (ROI2) using the second x-ray dose comprise an adjusted trajectory for both an x-ray source and an x-ray sensor based on the patient's maxillofacial second region of interest (ROI2).

19. A system for obtaining operating parameters for x-ray imaging a patient's maxillofacial region, comprising:

an x-ray source and at least one x-ray sensor that are configured to move around a patient's maxillofacial first region of interest while irradiating the latter with a slit-shaped x-ray beam formed from a first x-ray dose so as to acquire a first set of data relative to said patient's maxillofacial first region of interest when the patient is in an occlusion position or bites a patient positioning accessory, said patient's maxillofacial first region of interest including a horizontal plane that passes through the teeth and the bones of the jaw, said first set of data comprising a first set of x-ray images including the horizontal plane obtained at different angular positions relative to the patient's maxillofacial first region of interest (ROI1) and suitable for generating a CBCT slice; and a microprocessor configured to:
- reconstruct the CBCT slice comprising the horizontal plane based on the first set of data relative to the patient's maxillofacial first region of interest, and
- obtain operating parameters for an x-ray imaging apparatus based on the reconstructed CBCT slice in view of acquiring a second set of data of a patient's maxillofacial second region using a second x-ray dose, the first x-ray dose being lower than the second x-ray dose.

\* \* \* \* \*